United States Patent [19]

Kunz et al.

[11] Patent Number: 4,517,194
[45] Date of Patent: May 14, 1985

[54] AZOLYLMANDELIC ACID DERIVATIVES AND USE THEREOF FOR CONTROLLING MICROORGANISMS

[75] Inventors: Walter Kunz, Oberwil, Switzerland; Wolfgang Eckhardt, Lörrach, Fed. Rep. of Germany

[73] Assignee: Ciba-Geigy Corporation, Ardsley, N.Y.

[21] Appl. No.: 503,966

[22] Filed: Jun. 13, 1983

[30] Foreign Application Priority Data

Jun. 25, 1982 [CH] Switzerland ............... 3922/82

[51] Int. Cl.$^3$ ............ A01N 43/50; A01N 43/64; C07D 233/60; C07D 249/06
[52] U.S. Cl. ............... 514/184; 514/399; 514/189; 514/190; 514/383; 544/335; 544/405; 546/276; 546/278; 548/101; 548/262; 548/336; 548/341
[58] Field of Search .......... 548/262, 101, 341, 336; 544/335; 424/245, 269, 273 R, 251

[56] References Cited

U.S. PATENT DOCUMENTS

| | | | |
|---|---|---|---|
| 4,331,674 | 5/1982 | Kramer et al. | 424/269 |
| 4,366,152 | 12/1982 | Kramer et al. | 424/269 |
| 4,414,210 | 11/1983 | Miller et al. | 548/262 |
| 4,427,673 | 1/1984 | Kramer et al. | 424/269 |

FOREIGN PATENT DOCUMENTS 2640823 3/1977 Fed. Rep. of Germany ...... 548/262

*Primary Examiner*—Alton D. Rollins
*Attorney, Agent, or Firm*—Edward McC. Roberts; Frederick H. Rabin; Bruce M. Collins

[57] ABSTRACT

The invention relates to microbicidal mandelic acid derivatives of the formula I $$\begin{array}{c} R_1 \\ R_2 \\ R_3 \end{array}\!\!\!-\!\!\!Ar\!\!\!-\!\!\!\underset{R}{\overset{O-SO_2R_4}{\underset{|}{C}}}\!\!\!-\!\!\!CH_2-N\diagdown\overset{X=\!\!\!=}{\underset{=\!\!\!N}{|}}$$
(I)

wherein
X is the bridge member —CH= or —N=,
Ar is a phenyl, diphenyl or naphthyl group,
$R_1$, $R_2$ and $R_3$ independently of one another are hydrogen, nitro, halogen, $C_1$–$C_3$alkyl, $C_1$–$C_3$alkoxy or $C_1$–$C_3$haloalkyl,
R is one of the groups $$-COOR_5, -COSR_6, -CON\diagup\overset{R_7}{\underset{R_8}{\diagdown}} \text{ or } -CN,$$

$R_5$ is $C_2$–$C_{10}$alkenyl which is unsubstituted or substituted by halogen; $C_2$–$C_{10}$alkynyl which is unsubstituted or substituted by halogen; or is a $C_3$–$C_8$cycloalkyl group or a phenyl group which is unsubstituted or substituted; or is a $C_1$–$C_{12}$alkyl chain which from $C_2$alkyl may be interrupted by oxygen or sulfur and is unsubstituted or substituted by a member selected from the group consisting of halogen, phenyl, —COO—$C_1$–$C_4$alkyl, —CO—$C_1$–$C_4$alkyl, —CO-phenyl, an unsaturated or saturated 5- or 6-membered ring containing oxygen or sulfur as heteroatom, with each phenyl moiety being unsubstituted or substituted by one or more identical or different halogen atoms, is $C_1$–$C_{10}$alkyl, or is a phenyl or benzyl group, each unsubstituted or substituted
$R_4$ is $C_1$–$C_{12}$alkyl which is unsubstituted or substituted by halogen or $C_1$–$C_4$alkyl, or is phenyl or benzyl, each unsubstituted or substituted or is the —N($R_9$)($R_{10}$) group, wherein
$R_9$ is $C_1$–$C_6$alkyl and
$R_{10}$ is hydrogen, $C_1$–$C_4$alkyl, $C_1$–$C_4$haloalkylsulfenyl, —SC$_6$H$_5$ or —SC(CH$_3$)$_2$CN,
and the acid addition salts and metal complexes thereof.

25 Claims, No Drawings

AZOLYLMANDELIC ACID DERIVATIVES AND USE THEREOF FOR CONTROLLING MICROORGANISMS

The present invention relates to mandelic acid derivatives of the formula I below and to the agriculturally acceptable acid addition salts and metal complexes thereof. The invention further relates to the preparation of these compounds as well as to agrochemical compositions which contain at least one of the novel compounds as active ingredient. The invention also relates to the preparation of such compositions and to a method of controlling harmful microorganisms or of treating plants to prevent them from attack by such microorganisms.

Accordingly, the invention relates to compounds of the formula I

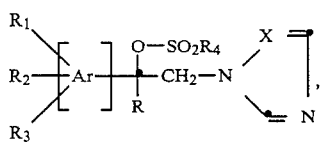

wherein

X is the bridge member —CH= or —N=,
Ar is a phenyl, diphenyl or naphthyl group,
$R_1$, $R_2$ and $R_3$ independently of one another are hydrogen, nitro, halogen, $C_1$–$C_3$alkyl, $C_1$=$C_3$alkoxy or $C_1$–$C_3$haloalkyl,
R is one of the groups

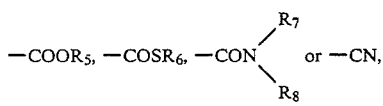

$R_5$ is $C_2$–$C_{10}$alkenyl which is unsubstituted or substituted by halogen; $C_2$–$C_{10}$alkynyl which is unsubstituted or substituted by halogen; or is a $C_3$–$C_8$cycloalkyl group or a phenyl group which is unsubstituted or substituted by halogen, $C_1$–$C_4$alkyl, $C_1$–$C_4$alkoxy, —CN or —CF$_3$; or is a $C_1$–$C_{12}$alkyl chain which from $C_2$alkyl may be interrupted by oxygen or sulfur and is unsubstituted or substituted by a member selected from the group consisting of halogen, phenyl, —COO—$C_1$–$C_4$alkyl, —CO—$C_1$–$C_4$alkyl, —CO—phenyl, an unsaturated or saturated 5- or 6-membered ring contining oxygen or sulfur as heteroatom, with each phenyl moiety being unsubstituted or substituted by one or more identical or different halogen atoms,
$R_6$ is $C_1$–$C_{10}$alkyl, or is a phenyl or benzyl group, each unsubstituted or substituted by halogen, $C_1$–$C_4$alkyl, $C_1$–$C_4$alkoxy, —CN, or —CF$_3$,
$R_7$ and $R_8$, each independently of the other, are hydrogen, $C_1$–$C_6$alkyl, $C_3$–$C_7$cycloalkyl, or a phenyl or benzyl group in each of which the aromatic ring is unsubstituted or substituted by halogen, $C_1$–$C_4$-alkyl, $C_1$–$C_4$alkoxy, —CN or —CF$_3$, or both taken together form a 5- or 6-membered saturated or unsaturated heterocyclic ring which may additionally contain 1 or 2 further N atoms,
$R_4$ is $C_1$–$C_{12}$alkyl which is unsubstituted or substituted by halogen or $C_1$–$C_4$alkyl, or is phenyl or benzyl, each unsubstituted or substituted by halogen, $C_1$–$C_4$alkyl, $C_1$–$C_4$alkoxy, $C_1$–$C_4$haloalkyl or cyano, or is the —N($R_9$)($R_{10}$) group, wherein
$R_9$ is $C_1$–$C_6$alkyl and
$R_{10}$ is hydrogen, $C_1$–$C_4$alkyl, $C_1$–$C_4$haloalkylsulfenyl, —SC$_6$H$_5$ or —SC(CH$_3$)$_2$CN, and the acid addition salts and metal complexes thereof.

Depending on the number of indicated carbon atoms, alkyl by itself or as moiety of another substituent comprises e.g. the following groups: methyl, ethyl, propyl, butyl, pentyl, hexyl, heptyl, octyl, nonyl, decyl, undecyl or dodecyl, and the isomers thereof, e.g. isopropyl, isobutyl, tert-butyl, isopentyl etc. Alkenyl is e.g. vinyl, propen-1-yl, allyl, buten-1-yl, buten-2-yl, buten-3-yl etc., as well as chains containing several double bonds. Alkynyl is e.g. propyn-1-yl, propargyl, butyn-1-yl, butyn-2-yl etc., with propargyl being preferred. Haloalkyl is in particular a monohalogenated to perhalogenated alkyl substituent, e.g. CHCl$_2$, CH$_2$Cl, CCl$_3$, CF$_3$, CH$_2$CH$_2$Cl etc. Throughout this specification, halogen denotes fluorine, chlorine, bromine or iodine, with chlorine, bromine or fluorine being preferred. Cycloalkyl is e.g. cyclopropyl, cyclobutyl, cyclopentyl, cyclohexyl, or cycloheptyl, eith cyclopropyl and cyclohexyl being preferred. Haloalkenyl is an alkenyl group which is substituted by one or more halogen atoms, e.g. chlorine and bromine, preferably chlorine. Furyl is preferably 2-furyl, tetrahydrofuryl, preferably 2-tetrahydrofuryl. Pyridyl is preferably pyrid-3- or -4-yl. Naphthyl is α- or β-naphthyl, preferably α-naphthyl. Examples of heterocyclic 5- or 6-membered rings containing up to 3 nitrogen atoms are pyrazole, imidazole, 1,2,4-triazole and 1,3,4-triazole, pyridine, pyrazine, pyrimidine, pyridazine, 1,3,5-triazine and 1,2,4-triazine.

Examples of salt-forming acids are inorganic acids, e.g. hydrohalic acids such as hydrofluoric acid, hydrochloric acid, hydrobromic acid, or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inoraganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals may exist in different valency states. The metal complexes of the formula I may be mononuclear or polynuclear, i.e. they can contain one or more prts of the organic molecule as ligands. Complexes with copper, zinc, manganese and tin are preferred.

The compounds of formula I are oils, resins or mainly solids which are stable at room temperature and have very valuable microbicidal properties. They can be used in agriculture or related fields preventively and curatively for controlling phytopathological microorganisms, for which utility the triazolylmethyl derivatives falling within the scope of formula I (X is N) are preferred. The compounds of formula I are very well tolerated by cultivated plants. The development of the plants is not impeded or retarded in any stage.

An important and preferred subgroup of compounds of the formula I comprises those of the formula I*

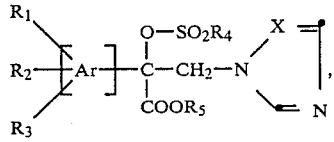
(I*)

wherein

X is the bridge member —CH= or —N=,

Ar is a phenyl, diphenyl or naphthyl group, $R_1$, $R_2$ and $R_3$, each independently of the other, are hydrogen, nitro, halogen, $C_1$–$C_3$alkyl, $C_1$–$C_3$alkoxy or $C_1$–$C_3$haloalkyl, $R_5$ is $C_1$–$C_4$alkyl, phenyl, or phenyl or benzyl, each substituted by one or more nitro groups, halogen atoms and/or methyl groups, $R_4$ is $C_1$–$C_6$alkyl, or phenyl or benzyl, each unsubstituted or substituted by fluorine, chlorine, bromine, $CF_3$, methyl, methoxy or cyano, or is —$N(R_9)(R_{10})$, wherein $R_9$ is $C_1$–$C_3$alkyl, and $R_{10}$ is hydrogen, $C_1$–$C_3$alkyl, —$SCCl_3$, —$SCCl_2F$, —$SCCl_2CHCl_2$, —$SC_6H_5$ or —$SC(CH_3)_2CN$, and the agriculturally suitable acid addition salts and metal complexes thereof.

A further preferred subgroup comprises compounds of formula I, wherein X is the bridge member —CH= or —N=; Ar is a phenyl group; $R_1$ in the ortho-position is hydrogen, nitro, halogen, $C_1$–$C_3$alkyl, $C_1$–$C_3$alkoxy, or $C_1$–$C_3$haloalkyl; $R_2$ in the para-position is hydrogen, nitro, halogen, $C_1$–$C_3$alkyl, $C_1$–$C_3$alkoxy or $C_1$–$C_3$haloalkyl; $R_3$ is hydrogen, methyl or halogen; R is a group

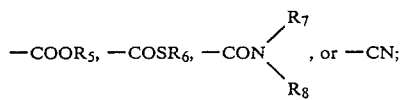

$R_5$ is $C_1$–$C_4$alkyl, phenyl, or phenyl or benzyl, each substituted by one or more nitro groups, halogen atoms and/or methyl groups; $R_6$ is $C_1$–$C_{10}$alkyl, or phenyl or benzyl, each unsubstituted or substituted by halogen, $C_1$–$C_4$alkyl, $C_1$–$C_4$alkoxy, —CN or —$CF_3$; each of $R_7$ and $R_8$ independently is hydrogen, $C_1$–$C_3$alkyl, $C_3$–$C_7$-cycloalkyl, phenyl or benzyl; and $R_4$ is $C_1$–$C_4$alkyl, or is phenyl or benzyl each unsubstituted or substituted by fluorine, chlorine, bromine, $CF_3$, methyl or methoxy, or is the —$N(R_9)(R_{10})$ group, wherein $R_9$ is $C_1$–$C_3$alkyl and $R_{10}$ is hydrogen, $C_1$–$C_3$alkyl, —$SCCl_3$, —$SCCl_2F$, —$SCCl_2CHCl_2$, —$SC_6H_5$ or —$SC(CH_3)_2CN$, and the acid additions salts and metal complexes thereof. This subgroup will be designated trhoughout as compounds I**.

Yet another particularly preferred subgroup comprises compounds of the formula I, when X is the bridge member —N=; the grouping

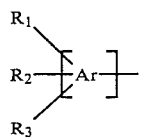

is a phenyl group which is substituted in the ortho- and/or para-position by nitro, fluorine, chlorine, bromine, methyl, methoxy and/or $CF_3$; R is the —$COOR_5$ group; $R_5$ is $C_1$–$C_4$alkyl, phenyl, or phenyl or benzyl, each substituted by nitro, chlorine, bromine, fluorine and/or methyl; and $R_4$ is methyl, ethyl, phenyl, p-tolyl, p-methylbenzyl, $NH(C_1$–$C_4)$-alkyl or —$N(R_9)(R_{10})$, wherein $R_9$ is $C_1$–$C_2$alkyl and $R_{10}$ is methyl, —$SCCl_3$, —$SCCl_2F$, —$SCCl_2CHCl_2$, —$SC_6H_5$ or —$SC(CH_3)_2CN$; and the acid addition salts and metal complexes thereof. This subgroup will be designated throughout as compounds I***.

The following individual compounds are particularly preferred microbicides:

ethyl 2-(1H-1,2,4-triazolylmethyl-1'-yl)-2-methylsulfonyloxy-2-chloro-4-bromophenylacetate, ethyl 2-(1H-1,2,4-triazolylmethyl-1'-yl)-2-methylsulfonyloxy-2,4-dichlorophenylacetate, ethyl 2-(1H-1,2,4-triazolylmethyl-1'-yl)-2-(N-methyl-N-fluorodichloromethanesulfenyl-sulfamoyloxy)-2-chloro-4-bromophenylacetate, methyl 2-(1H-1,2,4-triazolylmethyl-1'-yl)-2-(N-ethylsulfamoyloxy)-2,4-dichlorophenylacetate, ethyl 2-(1H-1,2,4-triazolylmethyl-1'-yl)-2-(N-methylsulfamoyloxy)-2-chloro-4-bromophenylacetate, ethyl 2-(1H-1,2,4-triazolylmethyl-1'-yl)-2-(N,N-dimethylsulfamoyloxy)-2-chloro-4-bromophenylacetate, ethyl 2-(1H-1,2,4-triazolylmethyl-1'-yl)-2-methylsulfonyloxy-4-chlorophenylacetate, ethyl 2-(1H-1,2,4-triazolylmethyl-1'-yl)-2-(N-methylsulfamoyloxy)-4-chlorophenylacetate, ethyl 2-(1H-1,2,4-triazolylmethyl-1'-yl)-2-(N-methyl-N-fluorodichloromethanesulfenyl-sulfamoyloxy)-4-chlorophenylacetate, isopropyl 2-(1H-1,2,4-triazolylmethyl-1'-yl)-2-methylsulfonyloxy-2-chloro-4-bromophenylacetate, ethyl 2-(1H-1,2,4-triazolylmethyl-1'-yl)-2-ethylsulfonyloxy-2-chloro-4-bromophenylacetate, ethyl 2-(1H-1,2,4-triazolylmethyl-1'-yl)-2-chloromethylsulfonyloxy-2-chloro-4-bromophenylacetate, ethyl 2-(1H-1,2,4-triazolylmethyl-1'-yl)-2-p-tosyloxy-2-chloro-4-bromophenylacetate, ethyl 2-(1H-1,2,4-triazolylmethyl-1'-yl)-2-(N-trichloromethanesulfenylsulfamoyloxy)-2-chloro-4-bromophenylacetate, methyl 2-(1H-1,2,4-triazolylmethyl-1'-yl)-2-methylsulfonyloxy-2,4-dichlorophenylacetate, n-butyl 2-(1H-1,2,4-triazolylmethyl-1'-yl)-2-methylsulfonyloxy-2,4-dichlorophenylacetate.

Compounds 1.8, 1.34, 1.60 and 1.62 listed in the subsequent Tables 1 and 2 are most preferred.

The compounds of formula I are prepared by sulfonylating a corresponding alcohol of the formula II

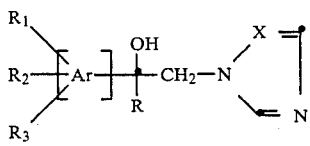

at the OH group with a sulfonyl halide of the formula XVI $$HalSO_2R_4 \qquad (XVI)$$

either direct or in the presence of an organic or inorganic base, or preferably by converting the alcohol of formula II, before the sulfonylation with XVI, first into an alkali alcoholate of the formula III

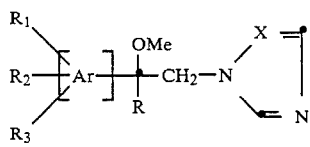

by reaction with an alkali metal hydride such as NaH, KH or the like, or with an alkaline organic compound such as butyl lithium, and, if desired, converting the resultant compound of the formula I into another compound of the formula I, and/or converting a free compound obtainable by the process into an acid addition salt, or converting an acid addition salt obtainable by the process into the free compound or into another acid addition salt, or converting a free compound or a salt obtainable by the process of the invention into a metal complex. In formulae II, III and XVI above, the substituents R, $R_1$, $R_2$, $R_3$, $R_4$, X and Ar are as defined for formula I, and Hal in formula XVI is a halogen atom, preferably a chlorine or bromine atom, and Me is an alkali metal atom such as lithium, potassium or sodium.

The reaction may be carried out in the absence, or preferably in the presence, of an inert solvent or diluent in the temperature range from −20° to +150° C. The direct sulfonylation of II with XVI is preferably carried out in the range from 0° to +40° C., and the indirect sulfonylation of III with XVI is preferably carried out in the range from 0° to +25° C.

Suitable inert solvents and diluents are aliphatic and aromatic hydrocarbons such as benzene, toluene, xylenes, petroleum ether, cyclohexane etc.; ether and etheral compounds such as dialkyl ethers (diethyl ether, diisopropyl ether, tert-butylmethyl ether etc.), anisole, dioxan, tetrahydrofuran, furan etc.; N-N-dialkylated amides such as dimethylformamide; dimethylsulfoxide; and, for the reaction of II with XVI, also halogenated aromatic and aliphatic hydrocarbons such as chlorobenzene, methylene chloride, ethylene, chloride, chloroform, carbon tetrachloride, tetrachloroethylene etc.; and, for both reactions, also mixtures of such solvents, with one another. In a particularly preferred embodiment of the sulfonylation of II with XVI, the reaction is carried out in a mixture of methylene chloride and triethylamine in the presence of a catalytic amount of 4-dimethylaminopyridine.

It can often be advantageous to carry out the reaction, or partial steps of a reaction, in an inert gas atmosphere and/or an absolute solvent. Suitable inert gases are e.g. nitrogen, helium, argon or, in certain cases, also carbon dioxide. The yield may also be improved by carrying out the reaction under elevated pressure, and/or by using absolute solvents.

Examples of suitable inorganic bases are oxides, hydrides, hydroxides, carbonates, carboxylic acid salts and alcoholates of alkaline earth metals, preferably of alkali metals, in particular those of sodium and potassium (e.g. NaH, NaOH, KOH, $Na_2CO_3$, $K_2CO_3$, $CaCO_3$, $CH_3COONa$, $C_2H_6COOK$, $C_2H_5ONa$, $CH_3ONa$ etc.), preferably the alkali metal hydrides such as NaH. Suitable organic bases are trialkylamines, e.g. triethylamine or other tertiary amines such as triethylenediamine, piperidine, pyridine, 4-dimethylaminopyridine, 4-pyrrolidylpyridine etc.

The intermediates and final products obtained by the preparatory methods of the invention can be isolated from the reaction medium and, if desired, purified by one of the methods conventionally employed, e.g. by extraction, crystallisation, chromatography, distillation etc. However, the reaction for obtaining the compounds of formula I may also be carried out continuously without isolation of the intermediates. Particularly advantageous variants of the process for obtaining the compounds of formula I and for preparing the intermediates, in particular those of formula II, are illustrated in a reaction scheme and subsequently described in detail.

In formulae Ia, Ib, II, III, IV, V, VI, VII, VIII, IX, X, XI, XII, XIII, XIV, XV and XVI, the substituents Ar, X, R, $R_1$, $R_2$, $R_3$, $R_4$, $R_5$, $R_6$, $R_7$ and $R_8$ are as defined for formula I.

Q in formula XV is either a customary leaving group, e.g. halogen, preferably chlorine, bromine or iodine, or is a sulfonyloxy group, preferably a benzenesulfonyloxy, p-tosyloxy or lower alkylsulfonyloxy group, preferably a mesyloxy group, or is an acyloxy group such as trifluoroacetyloxy. Q is also a hydroxy group or, according to "Synthesis 1979, pp. 561–569, is the radical

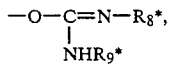

wherein $R_8^*$ and $R_9^*$ are organyl radicals, preferably lower alkyl or un-substituted or substituted phenyl radicals. M is hydrogen or a metal atom, preferably an alkali metal atom, most preferably sodium or potassium. Hal is halogen, preferably chlorine or bromine. Me is an alkali metal atom, preferably lithium, sodium or potassium.

The symbol α denotes the grouping

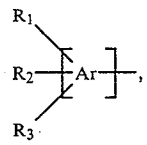

wherein the substituents $R_1$, $R_2$, $R_3$ and Ar are as defined for formula I.

Az is the following azolyl group

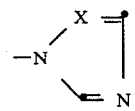

wherein X is —CH= or —N=.

Reaction scheme

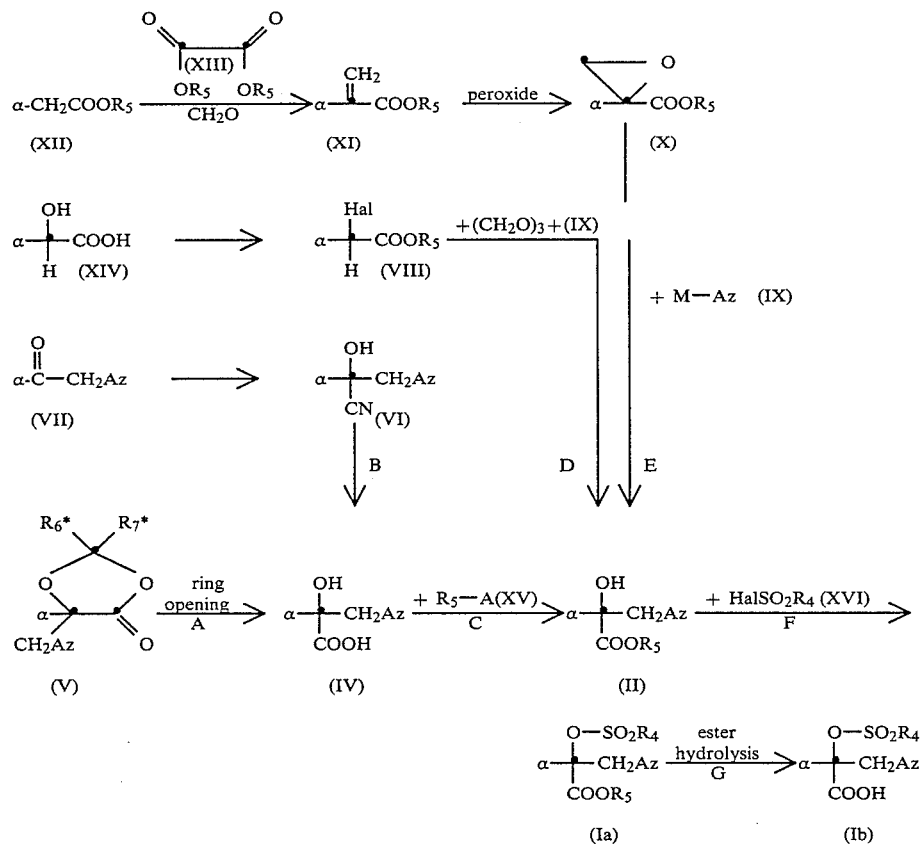

The procedure for preparing the intermediates as well as the compounds of the formula I is, in detail, as follows:

(i) Free α-hydroxycarboxylic acids (mandelic acids) of the formula IV are prepared by hydrolysing either, according to equation A, a dioxolanone of the formula V or, according to equation B, a cyanohydrin of the formula VI in basic or acid medium.

The hydrolysis reactions A and B are performed with acids or bases, advantageously in aqueous and/or alcoholic solutions, i.e. in polar solvents. The reactions can also be carried out in two-phase media, which case it is advantageous to add a customary phase-transfer catalyst. Inorganic and organic acids are suitable, e.g. mineral acids such as hydrohalic acids, sulfuric acid, phosphoric acid or sulfonic acids (p-toluenesulfonic acid, methanesulfonic acid). Suitable bases are organic and inorganic bases, e.g. oxides, hydrides, hydroxides, carbonates, carboxylic acid salts and alcoholates of alkaline earth metals and alkali metals, especially those of sodium and potassium.

The reaction temperature for the ring opening reaction A are in general from 0° to +140° C., preferably from +30° to +80° C., and for the hydrolysis of the cyanohydrin III from +60° to +140° C., preferably from +80° to +120° C., or for both reactions at the boiling point of the solvent or solvent mixture.

Most of the starting compounds of the formula II are known from EP Published Specification No. 44276. The novel compounds are prepared by methods corresponding to those described therein.

The mandelonitriles VI (variant B) can be prepared in conventional manner from aryl-azolylmethyl ketones of the formula VII

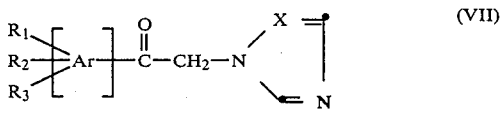

on the lines of a cyanohydrin synthesis, by reaction with HCN or an alkali cyanide, e.g. KCN or NaCN, at 0° to 100° C., advantageously in the presence of a trace of a base (preferably $NH_4OH$ or gaseous ammonia), or by way of the corresponding $NaHSO_3$ adduct VII [Org. Syntheses Coll. Vol. I, p. 336, or French patent specification No. 2,292,706; cf. also Houben Weyl "Methoden der organischen Chemie", Vol. 6/3, p 412].

Mandelonitriles VI can also be prepared in accordance with J. Org. Chem. 39,p. 914 (1974), by reaction of VII with trimethylsilyl cyanide, in the presence of catalytic amounts of $ZnI_2$, and subsequent hydrolysis of the adduct.

These nitriles may also be prepared by reaction of a ketone VII with a di-lower alkylcyanohydrin of the formula

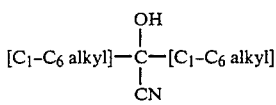

(alkyl is in particular methyl, ethyl or propyl), preferably in an inert solvent, or without a solvent, at 50°–150° C.

The hydrolysis of the nitriles VI to mandelic acid derivatives of the formula IV can be performed by methods similar to known methods, for example with concentrated hydrochloric acid [Houben-Weyl "Methoden der organischen Chemie", Vol.VIII, p. 427 et seq. (1952)].

Some of the ketones of formula VII used as intermediates are known from German Offenlegungsschrift No. 2 431 407 or from GB patent specification No. 1 464 224. Ketones of this type can also be obtained by hydrolysis from corresponding ketals, for example from those which are mentioned in any one of the following publications: German Offenlegungschrift specifications Nos. 2 610 022, 2 602 770, 2 930 029, 2 930 196 and 2 940 133.

Ketones of the formula VII which have not been described can be obtained by one of the aforementioned published methods.

(ii) Mandelic acid esters of the formula II can be prepared according to equation C, in conventional manner, by esterification of the corresponding mandelic acid derivative IV (also in the form of its alkali metal salt) with $R_5$—Q (XV) at $-20°$ to $+140°$ C. Aprotic solvents are preferred for this reaction. The direct esterification is advantageously performed with excess alcohol $R_5$—OH at 0° to 80° C. in the presence of a mineral acid, or preferably of a Lewis acid such as boron trifluoride etherate.

Compounds of the formula II can also be prepared according to equation D from an α-haloacetate of the formula VII with paraformaldehyde at 0° to 140° C., preferably at 10° to 80° C., and (a) with the desired azole of the formula IX (i.e. imidazole or triazole) in the presence of a base (e.g. NaOH), or (b) with an alkali metal salt of the azole of the formula IX in an anhydrous solvent (e.g. dimethylsulfoxide). The α-haloacetates of formula VIII can be obtained by conventional esterification of the corresponding acids XIV.

Esters of the formula II can also be prepared according to equation E from oxiranes of the formula X with an azole IX (M=H or alkali metal), in an inert, preferably polar, solvent (DMF, acetonitrile, DMSO and others, also in admixture with hydrocarbons), at 20° to 100° C. Inorganic or organic bases can be added in this reaction (cf. also EP published specification No. 15756).

As outlined in the reaction scheme, oxiranes of the formula X are obtainable by customary epoxidation (for e.g. $H_2O_2$/aqueous NaOH, peracetic acid) from corresponding alkenyl compounds of the formula XI. Compounds of the formula XI are produced from arylacetates of the formula XII by reaction with oxalates of the formula XIII and formaldehyde in the presence of a base [cf. Helvetica Chimica Acta 30, p.1349 (1947) and German Offenlegungsschrift No. 2 653 189].

Esters of the formula II can also be prepared from acids of the formula IV and dimethylformamide acetal (preferably in excess), the acetal component of which is intended to form the alcoholic part of the ester, in a solvent (e.g. a similar anhydrous alcohol or an ether) at 0° to 160° C. [Angew. Chemie 75, p. 296 (1963) and Helv. Chim. Acta 48, 1747 (1965)].

(iii) Compounds of formula I can also be converted in conventional manner into other compounds of formula I. Thus thioethers of formula I can be obtained from the corresponding free acids of formula I, e.g. by reaction with appropriate thioalcohols in aprotic solvents and preferably in the presence of weak bases.

The mandelic acid amides can in turn be obtained from esters or thioesters of the formula I with an excess of a corresponding amine. When $R_7$ and $R_8$ are closed to form a 5- or 6-membered ring, a heterocycle of this kind is introduced advantageously by reaction of the corresponding acid with 1,1′-carbonyldiazole or -diazine at 0° to 150° C., preferably in a solvent such as an ether or a halogenated hydrocarbon. Further conversion reactions are also possible.

(iv) The free hydroxyl group in compounds IV and II is, as described above, subjected to sulfonylation with sulfonyl halides of the formula XVI.

The other starting compounds of formulae III, IX, XII, XIII, XV and XVI are known or they can be obtained by methods which are known per se. The compound of formula I

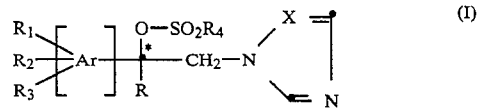

contain a centre of asymmetry (*) vicinal to the aromatic group Ar and to R, and can therefore be obtained in the form of two enantiomers. In general, a mixture of both enantiomers is obtained in the preparation of these compounds. This mixture can be resolved into the optical antipodes in conventional manner. Optically pure antipodes are obtained e.g. by variant B, in which the racemate of the formula IV is reacted with an optically active base to give the corresponding salt, which is isolated by fractional crystallisation and from which the optically pure acid of the formula IV is obtained. These acids can be converted, as illustrated in variant C, into the esters of the formula II. Sulfonylation of these esters yields optically pure compounds of the formula Ia which may be converted in consequent reactions into further compounds of formula I.

Unless otherwise specifically mentioned, reference to a compound of formula I will always be intended to mean a mixture of both enantiomers. Both antipodes have different microbicidal properties.

Surprisingly, it has been found that compounds of the formula I have for practical purposes a very useful microbicidal spectrum against phytopathogenic fungi and bacteria. They have very valuable curative, preventive and systemic properties and can be used for protecting cultivated plants. With the compounds of the formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms. The compounds of formula I are effective against the phytopathogenic fungi belonging to the following classes: Ascomycetes (e.g. Venturia, Podosphaera, Erysiphe, Monilinia, Uncinula); Basidomycetes (e.g. the genera Hemileia, Rhizoctonia, Pellicularia, Puccinia); *Fungi imperfecti* (e.g. Botrytis, Helminthosporium, Fusarium, Septoria, Cercospora, Piricularia and Alternaria) and against Phytomycetes such as Pythium. Compounds of formula I are also effective against phytopathogenic bacteria, in particular against the Xanthomonas species of the Pseudomonadaceae family. In addition, the compounds of formula I have a systemic action. They can also be used as seed dressing agents for protecting seeds (fruits, tubers, grains) and plant cuttings against fungus infections as well as against phytopathogenic microorganisms which occur in the soil. The compounds of the invention are also especially well tolerated by plants. Compounds of formula I also have microbicidal activity against species of fungi in the field of storage protection, e.g. against various mould fungi and some yeast fungi.

Accordingly, the invention also relates to microbicidal compositions and to the use of compounds of the formula I for controlling phytophatogenic microorganisms, especially parasitic fungi, and for the preventive treatment of plants to protect them from attack by such microorganisms.

The invention further embraces the preparation of agrochemical compositions which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these prepartions, if desired together with further carriers, surfactants or application-promoting adjuvants customarily employed in the art of formulation. Particularly advantageous adjuvants are phospholipids of vegetable or animal origin. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha. The application of such compositions can be made direct to the plant or parts thereof (foliar application), or to the locus of the plant (soil application), or to the propagation parts, e.g. by seed application.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used. e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 1 to 99.9%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

EXAMPLE 1 Preparation of

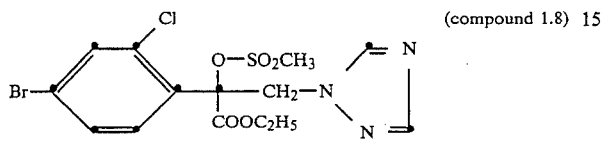
(compound 1.8)

Ethyl 2-(1H-1,2,4-triazolylmethyl-1'-yl)-2-methylsulfonyloxy-2-chloro-4-bromophenylacetate 1.8 g (0.04 mole) of a 55% dispersion of sodium hydride in paraffin oil is added to 50 ml of tetrahydrofuran and then a solution of 15 g (0.04 mole) of ethyl 2-(1H-1,2,4-triazolylmethyl-1'-yl)-2-hydroxy-2-chloro-4-bromophenylacetate in 70 ml of tetrahydrofuran is added dropwise at room temperature under nitrogen. Two hours later, after hydrogen has ceased to evolve, 5.5 g (0.048 mole) of methanesulfonyl chloride are added dropwise at 0°–5° C. and the reaction mixture is stirred overnight at room temperature. After the reaction mixture has been concentrated in a water jet vacuum, the residue is taken up in diethyl ether and the solution is washed in succession with a solution of sodium carbonate and with water, dried over sodium sulfate, filtered and concentrated. The crude product is purified through a column of silica gel with diethyl ether, affording 7.7 g of ethyl 2-(1H-1,2,4-triazolylmethyl-1'-yl)-2-methylsulfonyloxy-2-chloro-4-bromophenylacetate with a melting point of 105°–113° C.

EXAMPLE 2 Preparation of

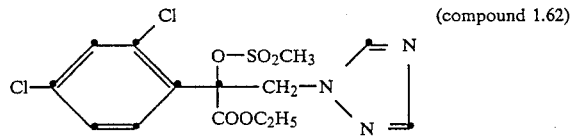
(compound 1.62)

Ethyl 2-(1H-1,2,4-triazolylmethyl-1'-yl)-2-methylsulfonyloxy-2,4-dichlorophenylacetate 6.6 g (0.02 mole) of ethyl 2-(1H-1,2,4-triazolylmethyl-1'-yl)-2-hydroxy-2,4-dichlorophenylacetate, 4.1 ml of triethylamine and 0.5 g of 4-dimethylaminopyridine are suspended in 40 ml of absolute dichloromethane. While cooling with ice, a solution of 2.5 ml of methanesulfonyl chloride in 10 ml of dichloromethane is stirred dropwise into this mixture over 15 minutes. The reaction mixture is stirred for 6 hours at room temperature, then cooled again with ice-water. Ice-water is added dropwise and the batch is extracted with dichloromethane. The combined extracts are washed with a small amount of bicarbonate solution and then with water, dried over sodium sulfate, filtered and concentrated. The residual oil is purified by chromatography through silica gel with a mixture of dichloromethane/isopropanol. Yield: 7.5 g (92.6% of theory) of ethyl 2-(1H-1,2,4-triazolyl-1'-yl)-2-methylsulfonyloxy-2,4-dichlorophenylacetate with a melting point of 119°–121° C.

EXAMPLE 3 Preparation of

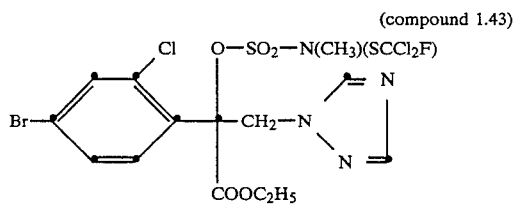
(compound 1.43)

Ethyl 2-(1H-1,2,4-triazolymethyl-1'-yl)-2-(N-methyl-N-fluorodichloromethanesulfenyl-sulfamoyloxy)-2-chloro-4-bromophenylacetate 6.1 g (0.013 mole) of ethyl 2-(1H-1,2,4-triazolylmethyl-1'-yl)-2-(N-methylsulfamoyloxy)-2-chloro-4-bromophenylacetate are dissolved in 100 ml of ethyl acetate and to this solution are added dropwise, in succession, 4.6 g (0.0273 mole) of fluorodichloromethanesulfenyl chloride and 2.9 g (0.0286 mole) of triethylamine at 0°–5° C. The reaction mixture is then stirred overnight at room temperature, then washed in succession with water, sodium carbonate solution and again with water, dried over sodium sulfate and concentrated, affording 8.1 g of the above compound in the form of a resinous substance with a melting point in the range from 40°–55° C.

EXAMPLE 4 Preparation of

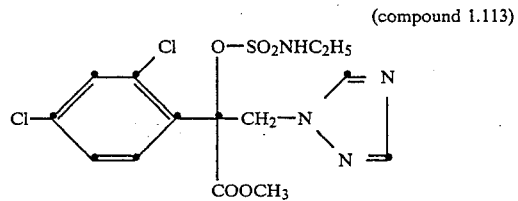
(compound 1.113)

Ethyl 2-(1H-1,2,4-triazolylmethyl-1'-yl)-2-(N-ethylsulfamoyloxy)-2,4-dichlorophenylacetate 6.2 g (0.02 mole) of ethyl 2-(1H-1,2,4-triazolylmethyl-1'-yl)-2-hydroxy-2,4-dichlorophenylacetate, 41 ml of triethylamine and 0.5 g of 4-dimethylaminopyridine are suspended in 40 ml of dichloromethane. While cooling with ice, 5 ml of ethylsulfamoyl chloride in 10 ml of dichloromethane are added dropwise over 20 minutes. The resultant solution is stirred for 20 hours at room temperature and then cooled to 0°–5° C. Ice-water is added and the mixture is then neutralised with bicarbonate solution and extracted with dichloromethane. The extracts are washed with water, dried, concentrated, and the residue is first recrystallised from tetrahydrofuran/hexane and then from ethyl acetate while filtering off hot a small amount of insoluble material.

Yield: 5.5 g (64% of theory) of the title compound with a melting point of 138°–141° C.

EXAMPLE 5 Preparation of (compound 1.39)

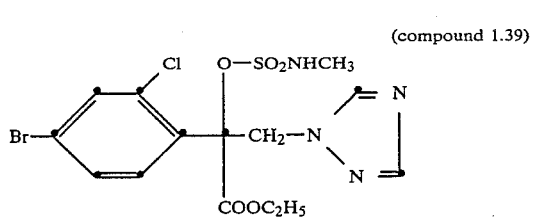

Ethyl 2-(1H-1,2,4-triazolylmethyl-1'-yl)-2-(N-methylsulfamoyloxy)-2-chloro-4-bromophenylacetate 4.4 g (0.1 mole) of a 55% dispersion of sodium hydride in paraffin oil are added to 50 ml of tetrahydrofuran under nitrogen and then 27.5 g (0.1 mole) of ethyl 2-(1H-1,2,4-triazolylmethyl-1'-yl)-2-hydroxy-2-chloro-4-bromophenylacetate in 130 ml of tetrahydrofuran are added dropwise at room temperature. After hydrogen has ceased to evolve, 16.9 g (0.12 mole) of methylsulfamoyl chloride are added dropwise at 0°–5° C. and the reaction mixture is stirred overnight at room temperature. The reaction mixture is concentrated in a water jet vacuum and the residue is dissolved in ethyl acetate and the solution is washed in succession with dilute sodium carbonate solution and water, dried over sodium sulfate, filtered and concentrated. The residue is crystallised by addition of diethyl ether, filtered and dried, affording 33 g of the title compound with a melting point of 130°–145° C.

EXAMPLE 6 Preparation of (compound 1.48)

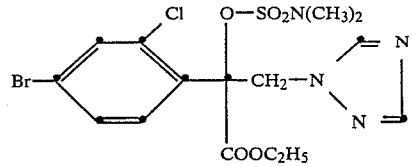

Ethyl 2-(1H-1,2,4-triazolylmethyl-1'-yl)-2-(N,N-dimethylsulfamoyloxy)-2-chloro-4-bromophenylacetate 1.3 g (0.03 mole) of a 55% dispersion of sodium hydride in paraffin oil are added to 30 ml of tetrahydrofuran under nitrogen and then 11.2 g (0.03 mole of ethyl 2-(1H-1,2,4-triazolylmethyl-1'-yl)-2-hydroxy-2-chloro-4-bromophenylacetate in 70 ml of tetrahydrofuran are added dropwise at room temperature. After hydrogen has ceased to evolve, 5.2 g (0.036 mole) of dimethylsulfamoyl chloride are added dropwise at 0°–5° C. and the reaction mixture is stirred overnight at room temperature. The reaction mixture is concentrated in a water jet vacuum and the residue is taken up in ethyl acetate. The ethyl acetate solution is washed in succession with ice-cold sodium carbonate solution and water, dried over sodium sulfate, filtered and concentrated. Paraffin oil is removed by dissolving the fresh residue in acetonitrile and passing the solution through a separating funnel. The acetonitrile solution is concentrated in vacuo, to give 11.3 g of the title compound in the form of a resinous substance.

The following compounds can be prepared in accordance with the foregoing Examples and the process variants described hereinbefore:

TABLE 1

Compounds of the formula

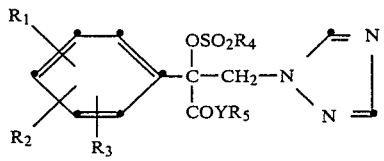

| Compound | $R_1$ | $R_2$ | $R_3$ | $R_4$ | $-YR_5$ | X | Physical data |
|---|---|---|---|---|---|---|---|
| 1.1 | H | H | H | $CH_3$ | $OC_2H_5$ | N | |
| 1.2 | H | H | H | $NHCH_3$ | $OC_2H_5$ | N | |
| 1.3 | H | H | H | $N(CH_3)SCCl_2F$ | $OC_2H_5$ | N | |
| 1.4 | 4-Cl | H | H | $CH_3$ | $OC_2H_5$ | N | m.p. 71–77° C. |
| 1.5 | 4-Cl | H | H | $NH-CH_3$ | $OC_2H_5$ | N | m.p. 85–99° C. |
| 1.6 | 4-Cl | H | H | $N(CH_3)SCCl_2F$ | $OC_2H_5$ | N | $n_D^{40}$ 1.5501 |
| 1.7 | 2-Cl | 4-Br | H | $CH_3$ | $OCH_3$ | N | |
| 1.8 | 2-Cl | 4-Br | H | $CH_3$ | $OC_2H_5$ | N | m.p. 105–113° C. |
| 1.9 | 2-Cl | 4-Br | H | $CH_3$ | $OC_3H_7(i)$ | N | $n_D^{40}$ 1.5430 |

TABLE 1-continued

Compounds of the formula

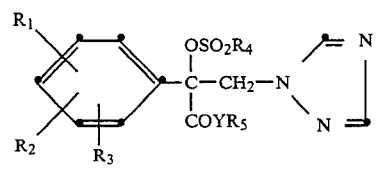

| Compound | $R_1$ | $R_2$ | $R_3$ | $R_4$ | $-YR_5$ | X | Physical data |
|---|---|---|---|---|---|---|---|
| 1.10 | 2-Cl | 4-Br | H | $CH_3$ | $O-C_6H_4Cl(4)$ | N | |
| 1.11 | 2-Cl | 4-Br | H | $CH_3$ | $SC_2H_5$ | N | |
| 1.12 | 2-Cl | 4-Br | H | $CH_3$ | $NHC_2H_5$ | N | |
| 1.13 | 2-Cl | 4-Br | H | $CH_3$ | NH—benzyl | N | |
| 1.14 | 2-Cl | 4-Br | H | $CH_3$ | $OCH_2$-(tetrahydropyran) | N | |
| 1.15 | 2-Cl | 4-Br | H | $CH_3$ | O—benzyl | N | |
| 1.16 | 2-Cl | 4-Br | H | $CH_3$ | $OCH_2CH=CH_2$ | N | |
| 1.17 | 2-Cl | 4-Br | H | $CH_3$ | $OCH_2C\equiv CH$ | N | |
| 1.18 | 2-Cl | 4-Br | H | $CH_3$ | $OCH_2$-(thiophene) | N | |
| 1.19 | 2-Cl | 4-Br | H | $CH_3$ | $NH_2$ | N | |
| 1.20 | 2-Cl | 4-Br | H | $CH_3$ | $OCH_3$ | CH | |
| 1.21 | 2-Cl | 4-Br | H | $CH_3$ | $OCH_2CH_2OCH_3$ | N | |
| 1.22 | 2-Cl | 4-Br | H | $NHCH_3$ | $OCH_2CH_2OCH_3$ | N | |
| 1.23 | 2-Cl | 4-Br | H | $N(SCCl_2F)(CH_3)$ | $OCH_2CH_2OCH_3$ | N | |
| 1.24 | 2-Cl | 4-Br | H | $N(SCCl_3)(CH_3)$ | $OCH_2CH_2OCH_3$ | N | |
| 1.25 | 2-Cl | 4-Br | H | $CH_3$ | $OCH_2CH_2Cl$ | N | |
| 1.26 | 2-Cl | 4-Br | H | $NHCH_3$ | $OCH_2CH_2Cl$ | N | |
| 1.27 | 2-Cl | 4-Br | H | $N(SCCl_2F)(CH_3)$ | $OCH_2CH_2Cl$ | N | |
| 1.28 | 2-Cl | 4-Br | H | $N(SCCl_3)(CH_3)$ | $OCH_2CH_2Cl$ | N | |
| 1.29 | 2-Cl | 4-Br | H | $CH_3$ | $-OCH(CH_3)COOCH_3$ | N | |
| 1.30 | 2-Cl | 4-Br | H | $CH_3$ | $-OCH_2SCH_3$ | N | |
| 1.31 | 2-Cl | 4-Br | H | $CH_3$ | $-OCH_2CO-C_4H_3-t$ | N | |
| 1.32 | 2-Cl | 4-Br | H | $CH_3$ | $-OCH_2OCH_3$ | N | |
| 1.33 | 2-Cl | 4-Br | H | $CH_3$ | $OC_{12}H_{25}(n)$ | N | |
| 1.34 | 2-Cl | 4-Br | H | $C_2H_5$ | $OC_2H_5$ | N | $n_D^{39}$ 1.5449 |
| 1.35 | 2-Cl | 4-Br | H | $C_3H_7(n)$ | $OC_2H_5$ | N | $n_D^{40}$ 1.5392 |
| 1.36 | 2-Cl | 4-Br | H | $CH_2Cl$ | $OC_2H_5$ | N | m.p. 50–65° C. |
| 1.37 | 2-Cl | 4-Br | H | $C_6H_4CH_3(4)$ | $OC_2H_5$ | N | m.p. 50–70° C. |
| 1.38 | 2-Cl | 4-Br | H | $-CH_2C_6H_4CH_3(4)$ | $OC_2H_5$ | N | |
| 1.39 | 2-Cl | 4-Br | H | $NHCH_3$ | $OC_2H_5$ | N | m.p. 130–145° C. |

TABLE 1-continued

Compounds of the formula

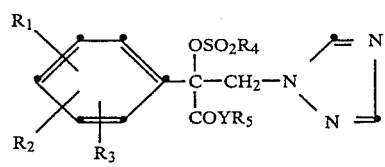

| Compound | R₁ | R₂ | R₃ | R₄ | —YR₅ | X | Physical data |
|---|---|---|---|---|---|---|---|
| 1.40 | 2-Cl | 4-Br | H | NHC$_2$H$_5$ | OC$_2$H$_5$ | N | m.p. 126–130° C. |
| 1.41 | 2-Cl | 4-Br | H | NHC$_3$H$_7$(n) | OC$_2$H$_5$ | N | |
| 1.42 | 2-Cl | 4-Br | H | NHC$_4$H$_9$(n) | OC$_2$H$_5$ | N | |
| 1.43 | 2-Cl | 4-Br | H | N(CH$_3$)(SCCl$_2$F) | OC$_2$H$_5$ | N | m.p. 40–55° C. |
| 1.44 | 2-Cl | 4-Br | N | N(CH$_3$)(SCCl$_3$) | OC$_2$H$_5$ | N | m.p. 55–65° C. |
| 1.45 | 2-Cl | 4-Br | H | N(CH$_3$)(S—C$_6$H$_5$) | OC$_2$H$_5$ | N | |
| 1.46 | 2-Cl | 4-Br | H | N(CH$_3$)(SCCl$_2$CHCl$_2$) | OC$_2$H$_5$ | N | |
| 1.47 | 2-Cl | 4-Br | H | N(CH$_3$)(S—C(CH$_3$)$_2$—CN) | OC$_2$H$_5$ | N | |
| 1.48 | 2-Cl | 4-Br | H | N(CH$_3$)$_2$ | OC$_2$H$_5$ | N | $n_D^{39}$ 1.5379 |
| 1.49 | 2-Cl | 4-Br | H | CH$_3$ | OC$_2$H$_5$ | CH | m.p. 51–77° C. |
| 1.50 | 2-Cl | 4-Br | H | NHCH$_3$ | OC$_2$H$_5$ | CH | |
| 1.51 | 2-Cl | 4-Br | H | N(CH$_3$)(SCCl$_3$) | OC$_2$H$_5$ | CH | |
| 1.52 | 2-Cl | 4-Br | H | N(C$_2$H$_5$)(SCCl$_2$F) | OC$_2$H$_5$ | N | $n_D^{39}$ 1.5419 |
| 1.53 | 2-Cl | 4-Br | H | N(C$_2$H$_5$)(SCCl$_3$) | OC$_2$H$_5$ | N | $n_D^{41}$ 1.5650 |
| 1.54 | 2-Cl | 4-Br | H | C$_4$H$_9$(n) | OC$_2$H$_5$ | N | |
| 1.55 | 2-Cl | 4-Br | H | C$_{12}$H$_{25}$(n) | OC$_2$H$_5$ | N | |
| 1.56 | 2-Cl | 4-Br | H | C$_2$H$_5$ | OC$_3$H$_7$(i) | N | |
| 1.57 | 2-Cl | 4-Br | H | CH$_3$ | OC$_4$H$_9$(n) | N | |
| 1.58 | 2-Cl | 4-Br | H | CH$_3$ | O—C$_6$H$_{11}$ | N | |

TABLE 1-continued

Compounds of the formula

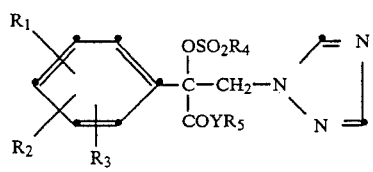

| Compound | R₁ | R₂ | R₃ | R₄ | —YR₅ | X | Physical data |
|---|---|---|---|---|---|---|---|
| 1.59 | 2-Cl | 4-Br | H | CH₃ | OCH₂—△ | N | |
| 1.60 | 2-Cl | 4-Cl | H | CH₃ | OCH₃ | N | m.p. 168–170° C. |
| 1.61 | 2-Cl | 4-Cl | H | CH₃ | OCH₃ | CH | |
| 1.62 | 2-Cl | 4-Cl | H | CH₃ | OC₂H₅ | N | m.p. 119–121° C. |
| 1.63 | 2-Cl | 4-Cl | H | CH₃ | OC₂H₅ | CH | |
| 1.64 | 2-Cl | 4-Cl | H | CH₃ | OC₃H₇(n) | N | |
| 1.65 | 2-Cl | 4-Cl | H | CH₃ | OC₃H₇(i) | N | |
| 1.66 | 2-Cl | 4-Cl | H | CH₃ | OC₄H₉(n) | N | $n_D^{54}$ 1.5262 |
| 1.67 | 2-Cl | 4-Cl | H | CH₃ | OC₁₂H₂₅(n) | N | |
| 1.68 | 2-Cl | 4-Cl | H | CH₃ | OCH₂—△ | N | |
| 1.69 | 2-Cl | 4-Cl | H | CH₃ | OCH₂CH₂Cl | N | |
| 1.70 | 2-Cl | 4-Cl | H | CH₃ | OCH₂CH₂OCH₃ | N | |
| 1.71 | 2-Cl | 4-Cl | H | CH₃ | OCH₂OCH₃ | N | |
| 1.72 | 2-Cl | 4-Cl | H | CH₃ | OCH₂SCH₃ | N | |
| 1.73 | 2-Cl | 4-Cl | H | CH₃ | OCH₂CH₂SCH₃ | N | |
| 1.74 | 2-Cl | 4-Cl | H | CH₃ | O—(cyclopentyl) | N | |
| 1.75 | 2-Cl | 4-Cl | H | CH₃ | O—(cyclohexyl) | N | |
| 1.76 | 2-Cl | 4-Cl | H | CH₃ | O—benzyl | N | |
| 1.77 | 2-Cl | 4-Cl | H | CH₃ | O—C₆H₄Cl(4) | N | |
| 1.78 | 2-Cl | 4-Cl | H | CH₃ | OCH₂CH=CH₂ | N | |
| 1.79 | 2-Cl | 4-Cl | H | CH₃ | OCH₂C≡CH | N | |
| 1.80 | 2-Cl | 4-Cl | H | CH₃ | OCH(CH₃)COOCH₃ | N | |
| 1.81 | 2-Cl | 4-Cl | H | CH₃ | OCH₂—(thienyl, S) | N | |
| 1.82 | 2-Cl | 4-Cl | H | CH₃ | O—(1,3-dioxan) | N | |
| 1.83 | 2-Cl | 4-Cl | H | CH₃ | —N(pyrazolyl) | N | |

TABLE 1-continued

Compounds of the formula

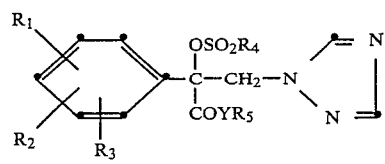

| Compound | $R_1$ | $R_2$ | $R_3$ | $R_4$ | $-YR_5$ | X | Physical data |
|---|---|---|---|---|---|---|---|
| 1.84 | 2-Cl | 4-Cl | H | $CH_3$ | −N⟨ (pyrrolidine) | N | |
| 1.85 | 2-Cl | 4-Cl | H | $CH_3$ | $OCH_2CCl_3$ | N | |
| 1.86 | 2-Cl | 4-Cl | H | $CH_3$ | $-S-C_6H_4C_4H_9-t(4)$ | N | |
| 1.87 | 2-Cl | 4-Cl | H | $CH_3$ | $-OCH(C_3H_7(i))_2$ | N | |
| 1.88 | 2-Cl | 4-Cl | | | $NH_2$ | N | |
| 1.89 | 2-Cl | 4-Cl | H | $CH_3$ | $NHC_2H_5$ | N | |
| 1.90 | 2-Cl | 4-Cl | H | $CH_3$ | $-NH-C_6H_5$ | N | |
| 1.91 | 2-Cl | 4-Cl | H | $C_2H_5$ | $-O-C_6H_4Cl(4)$ | N | |
| 1.92 | 2-Cl | 4-Cl | H | $CH_3$ | $-NH-$benzyl | N | |
| 1.93 | 2-Cl | 4-Cl | H | $C_3H_7-n$ | $-S-C_6H_4CH_3(4)$ | N | |
| 1.94 | 2-Cl | 4-Cl | H | $C_4H_9-n$ | $-O-C_4H_9-t$ | N | |
| 1.95 | 2-Cl | 4-Cl | H | $CH_3$ | $SC_2H_5$ | N | |
| 1.96 | 2-Cl | 4-Cl | H | $CH_3$ | $SCH_2-C_6H_5$ | N | |
| 1.97 | 2-Cl | 4-Cl | H | $C_2H_5$ | $OCH_3$ | N | |
| 1.98 | 2-Cl | 4-Cl | H | $C_2H_5$ | $OCH_5$ | N | |
| 1.99 | 2-Cl | 4-Cl | H | $C_2H_5$ | $OC_3H_7(i)$ | N | |
| 1.100 | 2-Cl | 4-Cl | H | $C_2H_5$ | $OC_4H_9(n)$ | N | |
| 1.101 | 2-Cl | 4-Cl | H | $CH_2Cl$ | $OCH_3$ | N | |
| 1.102 | 2-Cl | 4-Cl | H | $C_3H_7(n)$ | $OCH_3$ | N | |
| 1.103 | 2-Cl | 4-Cl | H | $C_4H_9(n)$ | $OCH_3$ | N | |
| 1.104 | 2-Cl | 4-Cl | H | $-C_6H_4-CH_3$ | $OCH_3$ | N | |
| 1.105 | 2-Cl | 4-Cl | H | $-CH_2-C_6H_4-CH_3$ | $OCH_3$ | N | |
| 1.106 | 2-Cl | 4-Cl | H | $-C_3H_7(i)$ | $OCH_3$ | N | |
| 1.107 | 2-Cl | 4-Cl | H | $-NHCH_3$ | $OCH_3$ | N | |
| 1.108 | 2-Cl | 4-Cl | H | $N(SCCl_2F)(CH_3)$ | $OCH_3$ | N | |
| 1.109 | 2-Cl | 4-Cl | H | $N(SCCl_3)(CH_3)$ | $OCH_3$ | N | |
| 1.110 | 2-Cl | 4-Cl | H | $N(S-C_6H_5)(CH_3)$ | $OCH_3$ | N | |

TABLE 1-continued

Compounds of the formula

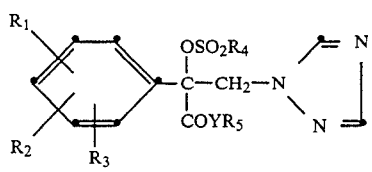

| Compound | R₁ | R₂ | R₃ | R₄ | —YR₅ | X | Physical data |
|---|---|---|---|---|---|---|---|
| 1.111 | 2-Cl | 4-Cl | H | SCCl₂CHCl₂, N-CH₃ | OCH₃ | N | |
| 1.112 | 2-Cl | 4-Cl | H | S—C(CH₃)(CH₃)—CN, N-CH₃ | OCH₃ | N | |
| 1.113 | 2-Cl | 4-Cl | H | NHC₂H₅ | OCH₃ | N | m.p. 138–141° C. |
| 1.114 | 2-Cl | 4-Cl | H | SCCl₂F, N-C₂H₅ | OCH₃ | N | |
| 1.115 | 2-Cl | 4-Cl | H | SCCl₃, N-C₂H₅ | OCH₃ | N | |
| 1.116 | 2-Cl | 4-Cl | H | NHC₃H₇(n) | OCH₃ | N | |
| 1.117 | 2-Cl | 4-Cl | H | NHC₄H₉(n) | OCH₃ | N | |
| 1.118 | 2-Cl | 4-Cl | H | NHCH₃ | OC₂H₅ | N | |
| 1.119 | 2-Cl | 4-Cl | H | SCCl₂F, N-CH₃ | OC₂H₅ | N | |
| 1.120 | 2-Cl | 4-Cl | H | SCCl₃, N-CH₃ | OC₂H₅ | N | |
| 1.121 | 2-Cl | 4-Cl | H | NHC₂H₅ | OC₂H₅ | N | |
| 1.122 | 2-Cl | 4-Cl | H | NHC₂H₅ | OC₃H₇(n) | N | |
| 1.123 | 2-Cl | 4-Cl | H | NHC₂H₅ | OC₄H₉(n) | N | |
| 1.124 | 2-Cl | 4-Cl | H | NHCH₃ | SC₂H₅ | N | |
| 1.125 | 2-Cl | 4-Cl | H | NHCH₃ | N(CH₃)₂ | N | |
| 1.126 | 2-Cl | 4-Cl | H | CH₃ | OCH₂COC₄H₉(t) | N | |
| 1.127 | 2-Cl | 4-Cl | H | CH₃ | OCH₂CO—C₆H₃Cl₂(2,4) | N | |
| 1.128 | 2-Cl | 4-Cl | H | NHCH₃ | OC₃H₇(i) | N | |
| 1.129 | 2-Cl | 4-Cl | H | NHCH₃ | OCH₃ | CH | |
| 1.130 | 2-Cl | 4-Cl | H | NHCH₃ | OC₄H₉(n) | N | |
| 1.131 | 2-Cl | 4-Cl | H | C₂H₅ | O—C₆H₅ | N | |
| 1.132 | 3-Cl | 4-Cl | H | CH₃ | OC₂H₅ | N | |
| 1.133 | 3-Cl | 4-Cl | H | C₂H₅ | OC₂H₅ | N | |
| 1.134 | 3-Cl | 4-Cl | H | NHCH₃ | OC₂H₅ | N | |
| 1.135 | 3-Cl | 4-Cl | H | SCCl₂F, N-CH₃ | OC₂H₅ | N | |

TABLE 1-continued

Compounds of the formula

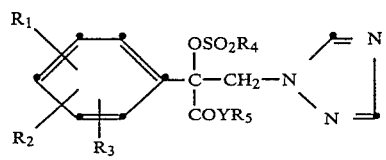

| Compound | R₁ | R₂ | R₃ | R₄ | —YR₅ | X | Physical data |
|---|---|---|---|---|---|---|---|
| 1.136 | 2-Cl | 4-Cl | 6-Cl | CH₃ | OC₂H₅ | N | |
| 1.137 | 2-Cl | 4-Cl | 6-Cl | C₂H₅ | OC₂H₅ | N | |
| 1.138 | 2-Cl | 4-Cl | 6-Cl | NHCH₃ | OC₂H₅ | N | |
| 1.139 | 2-Cl | 4-Cl | 6-Cl | N(CH₃)SCCl₂F | OC₂H₅ | N | |
| 1.140 | 2-Cl | 4-Cl | 6-Cl | N(CH₃)SCCl₃ | OC₂H₅ | N | |
| 1.141 | 2-Br | 4-Br | H | CH₃ | OC₂H₅ | N | m.p. 40–52° C. |
| 1.142 | 2-Br | 4-Br | G | C₂H₅ | OC₂H₅ | N | |
| 1.143 | 2-Br | 4-Br | H | NHCH₃ | OC₂H₅ | N | m.p. 140–144° C. |
| 1.144 | 2-Br | 4-Br | H | N(CH₃)SCCl₂F | OC₂H₅ | N | |
| 1.145 | 2-Br | 4-Br | H | N(CH₃)SCCl₃ | OC₂H₅ | N | |
| 1.146 | 4-Br | H | H | CH₃ | OCH₃ | N | |
| 1.147 | 4-Br | H | H | C₂H₅ | OCH₃ | N | |
| 1.148 | 4-Br | H | H | NHCH₃ | OCH₃ | N | |
| 1.149 | 2-Cl | 4-F | H | CH₃ | OCH₃ | N | |
| 1.150 | 2-Cl | 4-F | H | CH₃ | OC₂H₅ | N | |
| 1.151 | 2-Cl | 4-F | H | CH₃ | OC₃H₇(i) | N | |
| 1.152 | 2-Cl | 4-F | H | CH₃ | OC₄H₉(n) | N | |
| 1.153 | 2-Cl | 4-F | H | C₂H₅ | OCH₃ | N | |
| 1.154 | 2-Cl | 4-F | H | C₂H₅ | OC₂H₅ | N | |
| 1.155 | 2-Cl | 4-F | H | NHCH₃ | OC₂H₅ | N | |
| 1.156 | 2-Cl | 4-F | H | NHCH₃ | OCH₃ | N | |
| 1.157 | 2-Cl | 4-F | H | N(CH₃)SCCl₂F | OCH₃ | N | |
| 1.158 | 2-Cl | 4-F | H | NHC₂H₅ | OCH₃ | N | |
| 1.159 | 2-Cl | 4-F | H | NHC₃H₇(n) | OCH₃ | N | |
| 1.160 | 2-Cl | 4-F | H | NHC₄H₉(n) | OCH₃ | N | |
| 1.161 | 2-Cl | 4-F | H | C₄H₉(n) | OCH₃ | N | |
| 1.162 | 2-Cl | 4-F | G | CH₃ | (phenyl-H) | N | |
| 1.163 | 2-Cl | 4-F | H | CH₃ | OCH₂CH₂OCH₃ | N | |
| 1.164 | 2-Cl | 4-F | H | CH₃ | OCH₂CH₂Cl | N | |
| 1.165 | 2-Cl | 4-F | G | CH₃ | SC₂H₅ | N | |
| 1.166 | 2-Cl | 4-F | H | CH₃ | NH₂ | N | |

TABLE 1-continued

Compounds of the formula

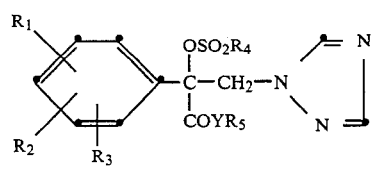

| Compound | $R_1$ | $R_2$ | $R_3$ | $R_4$ | $-YR_5$ | X | Physical data |
|---|---|---|---|---|---|---|---|
| 1.167 | 2-Cl | 4-F | H | $CH_3$ | $OCH_2-$<benzene> | N | |
| 1.168 | 2-$CH_3$ | 5-$CH_3$ | H | $CH_3$ | $OCH_3$ | N | |
| 1.169 | 3-$CF_3$ | H | H | $CH_3$ | $OCH_3$ | N | |
| 1.170 | 3-$NO_2$ | H | H | $CH_3$ | $OCH_3$ | N | |
| 1.171 | 4-CN | H | H | $CH_3$ | $OCH_3$ | N | |
| 1.172 | 4-$CH_3O$ | H | H | $CH_3$ | $OCH_3$ | N | |
| 1.173 | 2-Cl | 4-F | H | $CH_3$ | $OCH_3$ | CH | |
| 1.174 | 2-Cl | 4-Cl | H | $N(CH_3)_2$ | $OCH_3$ | N | |
| 1.175 | 2-Cl | 4-Cl | H | $-CH_3$ | $-O-C(CH_3)_3$ | N | |
| 1.176 | 2-Cl | 4-Cl | H | $-NHC_2H_5$ | $-OC(CH_3)_3$ | N | |
| 1.177 | 2-Cl | 4-Cl | H | $-N(C_2H_5)(SCCl_2F)$ | $-O-C(CH_3)_3$ | N | |
| 1.178 | 2-Cl | 4-Cl | H | $-NHC_2H_5$ | $-O-CH_2CH=CH_2$ | N | |
| 1.179 | 2-Br | 4-Br | H | $CH_3$ | $-OC_3H_7-1$ | N | m.p. 50–55° C. |

TABLE 2

Compounds of the formula

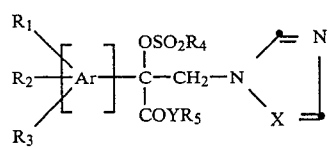

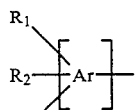

| Compound | $R_3$ | $R_4$ | $YR_5$ | X | Physical data |
|---|---|---|---|---|---|
| 2.1 | 4-biphenyl | $CH_3$ | $OCH_3$ | N | |
| 2.2 | 4-biphenyl | $CH_3$ | $OCH_3$ | CH | |
| 2.3 | 4-biphenyl | $CH_3$ | $OC_2H_5$ | N | |
| 2.4 | 4-biphenyl | $C_2H_5$ | $OCH_3$ | N | |
| 2.5 | 4-biphenyl | $NHCH_3$ | $OCH_3$ | N | |
| 2.6 | 4-biphenyl | $NHC_2H_5$ | $OCH_3$ | N | |
| 2.7 | 4-biphenyl | $N(SCCl_2F)(CH_3)$ | $OCH_3$ | N | |
| 2.8 | 4-biphenyl | $CH_3$ | $SC_2H_5$ | N | |
| 2.9 | 4-biphenyl | $CH_3$ | $O-C_6H_4Cl(4)$ | N | |
| 2.10 | 4-biphenyl | $CH_3$ | $NHC_2H_5$ | N | |
| 2.11 | 4-biphenyl | $CH_3$ | $OCH_2CH=CH_2$ | N | |
| 2.12 | 4-biphenyl | $CH_3$ | $OCH_2=CH$ | N | |
| 2.13 | 4-biphenyl | $CH_3$ | $O-C(CH_3)_3$ | N | |
| 2.14 | 4-biphenyl | $CH_3$ | $NH-N(CH_3)_2$ | N | |

TABLE 2-continued

Compounds of the formula

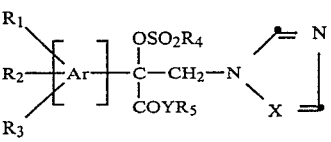

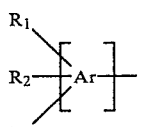

| Compound | R₃ | R₄ | YR₅ | X | Physical data |
|---|---|---|---|---|---|
| 2.15 | Br—⟨phenyl-phenyl⟩— | CH₃ | OCH₃ | N | |
| 2.16 | Br—⟨phenyl-phenyl⟩— | CH₃ | O—⟨phenyl⟩—H | N | |
| 2.17 | α-naphthyl | CH₃ | OCH₃ | N | |
| 2.18 | α-naphthyl | NH—CH₃ | OCH₃ | N | |
| 2.19 | α-naphthyl-2-CH₃ | CH₃ | OCH₃ | N | |
| 2.20 | β-naphthyl | CH₃ | OCH₃ | N | |
| 2.21 | β-naphthyl | CH₃ | OC₂H₅ | N | |
| 2.22 | β-naphthyl | C₂H₅ | OCH₃ | N | |
| 2.23 | β-naphthyl | NHCH₃ | OCH₃ | N | |
| 2.24 | β-naphthyl | NHC₂H₅ | OCH₃ | N | |
| 2.25 | β-naphthyl | N(SCCl₃)(CH₃) | OCH₃ | N | |
| 2.26 | 4-phenoxyphenyl | CH₃ | OCH₃ | N | |
| 2.27 | 4-phenoxyphenyl | C₂H₅ | OC₂H₅ | N | |
| 2.28 | 4-phenoxyphenyl | CH₃ | OCH₃ | CH | |

FORMULATION EXAMPLES

FORMULATION EXAMPLES FOR ACTIVE INGREDIENTS OF THE FORMULA I (throughout, percentages are by weight)

| (A) Emulsifiable concentrates | (a) | (b) | (c) |
|---|---|---|---|
| a compound of Tables 1 and 2 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| (B) Solutions | (a) | (b) | (c) | (d) |
|---|---|---|---|---|
| a compound of Tables 1 and 2 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20 | — | — |
| epoxidised coconut oil | — | — | 1% | 5% |
| petroleum distillate (boiling range 160–190°) | — | — | 94% | — |

These solutions are suitable for application in the form of microdrops.

| (C) Granulates | (a) | (b) |
|---|---|---|
| a compound of Tables 1 and 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (D) Dusts | (a) | (b) |
|---|---|---|
| a compound of Tables 1 and 2 | 2% | 5% |
| highly dispersed silicic acid | 1%. | 5% |
| talcum | 97% | — |
| kaolin | — | 90% |

Ready-for-use dusts are obtained by intimately mixing the carriers with the active ingredient.

| (E) Wettable powders | (a) | (b) | (c) |
|---|---|---|---|
| a compound of Tables 1 and 2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

BIOLOGICAL EXAMPLES

EXAMPLE B1: Action against *Puccinia graminis* on wheat (a) Residual-protective action Wheat plants are treated 6 days after sowing with a spray mixture prepared from a wettable powder formulation of the active ingredient (0.06%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the active ingredient (0.006% based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation of rust pustule development is made 12 days after infection. Attack on untreated and infected control plants is 100%. Plants treated with compositions containing compounds of formula I exhibit only insignificant (<20%) or no attack. Compounds 1.4, 1.5, 1.6, 1.8, 1.9, 1.34–1.37, 1.39, 1.40, 1.43, 1.44, 1.48, 1.49, 1.52, 1.60, 1.62, 1.66, 1.113, 1.141, 1.43 and 1.179 still inhibit fungus attack even when used in a concentration of 0.002%.

EXAMPLE B2: Action against *Cerocospora arachidicola* in groundnut plants Residual protective action Groundnut plants 10–15 cm in height are sprayed with a wettable powder containing 0.006% of active ingredient and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection, and is based on the number and size of the specks.

Compared with untreated and infected control plants (number and size of specks=100%), cercospora attack is significantly reduced on groundnut plants treated with compounds of Tables 1 and 2. For Example: compounds 1.8, 1.9, 1.34, 1.35, 1.36, 1.37, 1.39, 1.43, 1.44, 1.60, 1.62, 1.66, 1.113, 1.141 and 1.143 and others inhibit the occurrence of specks almost completely (0–10%) in the above tests.

EXAMPLE B3: Action against *Erysiphe graminis* on barley (a) Residual protective action Barley plants about 8 cm in height are sprayed with a spray mixture (0.02%) prepared from the active ingredient formulated as a wettable powder. The treated plants are dusted with conidia of the fungus after 3–4 hours. The infected barley plants are then stood in a greenhouse at about 22° C. The extent of the infestation is evaluated after 10 days.

(b) Systemic action

Barley plants about 8 cm in height are treated with a spray mixture (0.006%), based on the volume of the soil) prepared from the active ingredient formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days. Compounds of formula I and compounds of Tables 1 and 2 reduce fungus attack to less than 20%, whereas attack is 100% on untreated and infected control plants. Compounds 1.4, 1.5, 1.8, 1.9, 1.34–1.37, 1.39, 1.40, 1.43, 1.44, 1.49, 1.53, 1.60, 1.62, 1.66, 1.113, 1.141, 1.143 and 1.179 and others inhibit fungus attack completely (0–5%).

EXAMPLE B4: Residual-protective action against *Venturia inaequalis* on apple shoots Apple cuttings with 10–20 cm long fresh shoots are sprayed with a spray mixture prepared from a wettable powder formulation of the active ingredient with a conidia suspension of the fungus. The plants are then incubated for 5 days at 90–100% relative humidity and stood in a greenhouse for a further 10 days at 20°–24° C. Scab infestation is evaluated 15 days after infection. Compounds 1.8, 1.9, 1.36, 1.39, 1.43, 1.44, 1.60, 1.62, 1.66, 1.113 and 1.141 and other inhibit infestation to less than 10% and compounds 1.36 and 1.62 inhibit infestation completely. Shoots on apple trees in field trails are protected to the same extent without being inhibited in their development.

EXAMPLE B5: Action against *Botrytis cinerea* on beans Residual protective action Bean plants about 10 cm in height are sprayed with a spray mixture (0.02% concentration) prepared from the active ingredient formulated as wettable powder. After 48 hours, the treated plants are infected with a conidia suspension of the fungus. The infected plants are incubated for 2 to 3 days at 95–100% relative humidity and 21° C., and evaluation of the fungus attack is then made. Numerous compounds of Tables 1 and 2 inhibit fungus infection to less than 25%, e.g. compounds 1.8, 1.34, 1.35, 1.62, 1.66 and 1.141.

EXAMPLE B6: Action against Piricularia on rice Residual-protective action

After being reared for 2 weeks, rice plants are sprayed with a spray mixture (0.02%) prepared from a wettable powder formulation of the test compound. The treated plants are infected 48 hours later with a conidia suspension of the fungus. Fungus attack is evaluated after incubation for 5 days at 95–100% relative humidity and 24° C. Compared with 100% attack on unprotected plants, compounds of Tables 1 and 2 inhibit fungus infestation significantly. For example, compounds 1.8, 1.9, 1.39 and other inhibit Piricularia attack to less than 10%.

What is claimed is:

1. A compound selected from the group consisting of (i) a mandelic acid derivative of the formula

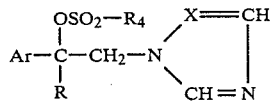

wherein

X is N or CH;

Ar is an aryl group selected from the group consisting of phenyl, biphenylyl and naphthyl which aryl group is unsubstituted or substituted with one, two or three like or different members selected from the group consisting of nitro, halo, alkyl of 1 to 3 carbon atoms, alkoxy of 1 to 3 carbon atoms, and haloalkoxy of 1 to 3 carbon atoms;

R is group of the formulae

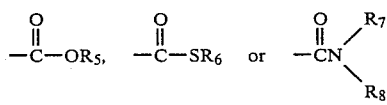

in which $R_5$ is alkyl of 1 to 4 carbon atom, phenyl or benzyl, said phenyl and benzyl groups being unsubstituted or substituted with nitro, halo or methyl, $R_6$ is alkyl of 1 to 3 carbon atoms; and each of $R_7$ and $R_8$ independently of the other is hydrogen, alkyl of 1 to 3 carbon atoms, cycloalkyl of 3 to 7 carbon atoms, phenyl or benzyl; and $R_4$ is alkyl of 1 to 6 carbon atoms, unsubstituted phenyl, unsubstituted benzyl, phenyl or benzyl substituted with halo, alkyl of 1 to 4 carbon atoms, alkoxy of 1 to 4 carbon atoms, haloalkoxy of 1 to 4 carbon atoms or cyano, or

in which $R_9$ is alkyl of 1 to 6 carbon atoms and $R_{10}$ is hydrogen, alkyl of 1 to 4 carbon atoms, haloalkylsulfenyl, —$SC_6H_5$ or —$SC(CH_3)_2CN$, and (ii) the acid addition salts and metal complexes thereof.

2. A compound according to claim 1 wherein said mandelic acid derivative has the formula

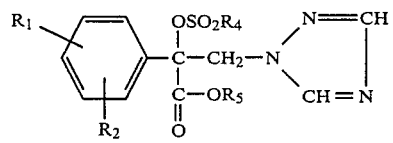

wherein $R_4$ is as therein defined;

each of $R_1$ and $R_2$, independently of the other, is selected from the group consisting of hydrogen, nitro, halo, alkyl of 1 to 3 carbon atoms, alkoxy of 1 to 3 carbon atoms, and haloalkoxy of 1 to 3 carbon atoms; and $R_5$ is alkyl of 1 to 3 carbon atoms, phenyl or benzyl, said phenyl and benzyl being unsubstituted or substituted with nitro, halo or methyl.

3. A compound according to claim 2 wherein $R_1$ is in the 4-position and $R_2$ is in the 2-position of the depicted phenyl group, and $R_4$ is methyl, ethyl, phenyl, 4-methylphenyl, 4-methylbenzyl, or

in which $R_9$ is methyl or ethyl, and $R_{10}$ is methyl, trichloromethylthio, fluorodichloromethylthio, phenylthio or 2-cyanoprop-2-ylthio.

4. A compound according to claim 1 wherein said mandelic acid derivative has the formula

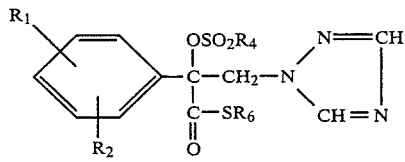

wherein $R_4$ is as therein defined;

each of $R_1$ and $R_2$, independently of the other, is selected from the group consisting of hydrogen, nitro, halo, alkyl of 1 to 3 carbon atoms, alkoxy of 1 to 3 carbon atoms, and haloalkoxy of 1 to 3 carbon atoms; and $R_6$ is alkyl of 1 to 3 carbon atoms.

5. A compound according to claim 4 wherein $R_1$ is in the 4-position and $R_2$ is in the 2-position of the depicted phenyl group, and $R_4$ is methyl, ethyl, phenyl, 4-methylphenyl, 4-methylbenzyl, or

in which $R_9$ is methyl or ethyl, and $R_{10}$ is methyl, trichloromethylthio, fluorodichloromethylthio, phenylthio or 2-cyanoprop-2-ylthio.

6. A compound according to claim 1 wherein said mandelic acid derivative has the formula

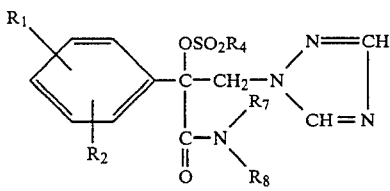

wherein
R₄ is as therein defined;
each of $R_1$ and $R_2$, independently of the other, is selected from the group consisting of hydrogen, nitro, halo, alkyl of 1 to 3 carbon atoms, alkoxy of 1 to 3 carbon atoms, and haloalkoxy of 1 to 3 carbon atoms; and
each of $R_7$ and $R_8$ is hydrogen or alkyl of 1 to 3 carbon atoms.

7. A compound according to claim 6 wherein $R_1$ is in the 4-position and $R_2$ is in the 2-position of the depicted phenyl group, and $R_4$ is methyl, ethyl, phenyl, 4-methylphenyl, 4-methylbenzyl, or

in which
$R_9$ is methyl or ethyl, and
$R_{10}$ is methyl, trichloromethylthio, fluorodichloromethylthio, phenylthio or 2-cyanoprop-2-ylthio.

8. A compound according to claim 1 wherein said mandelic acid derivative is ethyl 2-(1H-1,2,4-triazolylmethyl-1'-yl)-2-methylsulfonyloxy-2-chloro-4-bromophenylacetate.

9. A compound according to claim 12 wherein said mandelic acid derivative is ethyl 2-(1H-1,2,4-triazolylmethyl-1'-yl)-2-methylsulfonyloxy-2,4-dichlorophenylacetate.

10. A compound according to claim 1 wherein said mandelic acid derivative is ethyl 2-(1H-1,2,4-triazolylmethyl-1'-yl)-2-(N-methyl-N-fluorodichloromethanesulfenylsulfamoyloxy)-2-chloro-4-bromophenylacetate.

11. A compound according to claim 1 wherein said mandelic acid derivative is methyl 2-(1H-1,2,4-triazolylmethyl-1'-yl)-2-(N-ethylsulfamoyloxy)-2,4-dichlorophenylacetate.

12. A compound according to claim 1 wherein said mandelic acid derivative is ethyl 2-(1H-1,2,4-triazolylmethyl-1'-yl)-2-(N-methylsulfamoyloxy)-2-chloro-4-bromophenylacetate.

13. A compound according to claim 1 wherein said mandelic acid derivative is ethyl 2-(1H-1,2,4-triazolylmethyl-1'-yl)-2-(N,N-dimethylsulfamoyloxy)-2-chloro-4-bromophenylacetate.

14. A compound according to claim 1 wherein said mandelic acid derivative is ethyl 2-(1H-1,2,4-triazolylmethyl-1'-yl)-2-methylsulfonyloxy-4-chlorophenylacetate.

15. A compound according to claim 1 wherein said mandelic acid derivative is ethyl 2-(1H-1,2,4-triazolylmethyl-1'-yl)-2-(N-methylsulfamoyloxy)-4-chlorophenylacetate.

16. A compound according to claim 1 wherein said mandelic acid derivative is ethyl 2-(1H-1,2,4-triazolylmethyl-1'-yl)-2-(N-methyl-N-fluorodichloromethanesulfenylsulfamoyloxy)-4-chlorophenylacetate.

17. A compound according to claim 1 wherein said mandelic acid derivative is isopropyl 2-(1H-1,2,4-triazolylmethyl-1'-yl)-2-methylsulfonyloxy-2-chloro-4-bromophenylacetate.

18. A compound according to claim 1 wherein said mandelic acid derivative is ethyl 2-(1H-1,2,4-triazolylmethyl-1'-yl)-2-ethylsulfonyloxy-2-chloro-4-bromophenylacetate.

19. A compound according to claim 1 wherein said mandelic acid derivative is ethyl 2-(1H-1,2,4-triazolylmethyl-1'-yl)-2-chloromethylsulfonyloxy-2-chloro-4-bromophenylacetate.

20. A compound according to claim 1 wherein said mandelic acid derivative is ethyl 2-(1H-1,2,4-triazolylmethyl-1'-yl)-2-p-tosyloxy-2-chloro-4-bromophenylacetate.

21. A compound according to claim 1 wherein said mandelic acid derivative is ethyl 2-(1H-1,2,4-triazolylmethyl-1'-yl)-2-(N-trichloromethanesulfenylsulfamoyloxy)-2-chloro-4-bromophenylacetate.

22. A compound according to claim 1 wherein said mandelic acid derivative is methyl 2-(1H-1,2,4-triazolylmethyl-1'-yl)-2-methylsulfonyloxy-2,4-dichlorophenylacetate.

23. A compound according to claim 1 wherein said mandelic acid derivative is n-butyl 2-(1H-1,2,4-triazolylmethyl-1'-yl)-2-methylsulfonyloxy-2,4-dichlorophenylacetate.

24. A method of combatting fungal and bacterial attack on cultivated plants which comprises applying to the plants or their locus an effective amount of a compound according to claim 1.

25. A composition for combatting fungal and bacterial attack on cultivated plants which comprises an effective amount of a compound according to claim 1 and a carrier therefor.

* * * * *